US00PP10057P

United States Patent [19]

Fuess

[11] Patent Number: Plant 10,057

[45] Date of Patent: Oct. 7, 1997

[54] CHRYSANTHEMUM PLANT NAMED 'EMPIRE PEACH CHAMPAGNE'

[76] Inventor: Janet S. Fuess, 22 Country Club Dr., New York Mills, N.Y. 13417

[21] Appl. No.: 670,277

[22] Filed: Jun. 13, 1996

[51] Int. Cl.[6] ..... A01H 5/00

[52] U.S. Cl. ..... Plt./79

[58] Field of Search ..... Plt./78, 79, 76

[56] References Cited

U.S. PATENT DOCUMENTS

P.P. 6,920 7/1989 Fuess ..... Plt./76

4,616,099 10/1986 Sparkes ..... 47/58

OTHER PUBLICATIONS

Broertjes, et al., 1980, "A Mutant of a Mutant of a . . . Irradiation of Progressive Radiation–Induced Mutants in a Mutation Breeding Programme with *Chrysanthemum morifolium*", Euphytica, 29:525–530.

Gosling, ed., 1979, "The Chrysanthemum Manual—6th Edition", The National Chrysanthemum Society, London, Essex Telegraph Press, Ltd., pp. 329–336.

Broertjes, et al., 1978, "Application of Mutation Breeding Methods in the Improvement of Vegetatively Propagated Crops", Elsevier Sci. Pub. Co., New York, pp. 162–175.

Searle, et al., 1968, "Chrysanthemums the Year Round", Blanford Press, London, pp. 27–29, 320–327.

Chan, 1966, "Chrysanthemum and Rose Mutations Induced by X–rays", Am.Soc.Hort.Sci.Proc., pp. 613–620.

Broertjes, 1966, "Mutation Breeding of Chrysanthemums", Euphytica, 15:156–162.

Dowrick, et al., 1966, "The Induction of Mutations in Chrysanthemum Using X–and Gamma Radiation", Euphytica, 15:204–210.

*Primary Examiner*—Howard J. Locker

*Attorney, Agent, or Firm*—Foley & Lardner

[57] ABSTRACT

A new and distinct cultivar of Chrysanthemum plant named Empire Peach Champagne, characterized particularly by its peach ray florets, almost fully double flowers which are very resistant to shattering; compact, cushion habit; 6.0–8.0 cm capitulum diameter; a natural season flower date of September 20; and 7 week flower response in light/shade programs.

1 Drawing Sheet

The present invention comprises a new and distinct cultivar of Chrysanthemum plant, botanically known as *Dendranthema grandiflora*, and referred to by the cultivar name Empire Peach Champagne.

Empire Peach Champagne is a product of a mutation induction program. The new cultivar was discovered and selected by the inventor Janet S. Fuess in March 1993 in a controlled environment in New Hartford, N.Y. as one flowering plant within a flowering block established as rooted cuttings from stock plants which had been exposed as rooted cuttings to an X-ray source of 1270-1800 rads in Mulberry, Fla. on Jan. 7, 1993. The irradiated parent cultivar was Pink Champagne, disclosed in U.S. Plant Pat. No. 6,920 and described as a decorative garden mum with lavender pink color.

The irradiation program resulting in Empire Peach Champagne had as its primary objective the expansion of color ranges of the parent cultivar Pink Champagne. The irradiation program comprised irradiating of cuttings of the parent cultivar at radiation levels of a minimum of 1270 and a maximum of 1800 rads for 90 seconds. A total of 1375 cuttings harvested from a total of 500 irradiated plants were flowered on Mar. 8, 1993. Of these, 69 initial selections were made, which selections were then revegetated and reflowered on Aug. 28, 1993 and again Feb. 6, 1994. Twelve selections remained stable, and were flowered on May 22, 1994 and Sep. 18, 1994 before choosing the final 3 selections. These three varieties were further trialed in New Hartford, N.Y. and Oxnard, Calif., ultimately resulting in the decision to introduce one selection as Empire Royal Champagne, one as Empire Gold Champagne, both of which are disclosed in pending application Ser. No. 08/670,280 and 08/670,278, respectively, and one as Empire Peach Champagne.

The first act of asexual reproduction of Empire Peach Champagne was accomplished when vegetative cuttings were taken from the initial selection in June 1993 in a controlled environment in New Hartford, N.Y. by a technician working under formulations established and supervised by the inventor. Horticultural examination of selected units initiated in September 1993 has demonstrated that the combination of characteristics as herein disclosed for Empire Peach Champagne are firmly fixed and are retained through successive generations of asexual reproduction.

Empire Peach Champagne has not been observed under all possible environmental conditions. The phenotype may vary significantly with variations in environment such as temperature, light intensity, and day length, without, however, any variance in genotype. The following observations, measurements and comparisons describe plants grown in New Hartford, N.Y. under natural outdoor conditions which approximate those generally used in commercial practice.

The following traits have been repeatedly observed and are determined to be basic characteristics of Empire Peach Champagne which in combination distinguish this Chrysanthemum as a new and distinct cultivar:

1. Peach ray floret color.
2. Almost fully double flowers, with only a few disc florets present.
3. Flowers very resistant to shattering.
4. Fully expanded ray florets are approximately 30-35 mm long and 7-8 mm wide.
5. Average of 360 ray florets per capitulum.
6. Capitulum is 6-8 cm in diameter.
7. Seven (7) week flower response in light/shade programs.
8. Performs well in the outdoor garden, with a natural season flowering date of September 20 in New Hartford, N.Y.
9. Compact cushion habit, making it suitable for production in 4" up to 8" containers.

Of the many commercial cultivars known to the present inventor, the most similar in comparison to Empire Peach Champagne is the parent cultivar Pink Champagne.

In comparison to Pink Champagne, Empire Peach Champagne differs only in ray floret color, with Empire Peach Champagne having a peach flower color, compared to the lavender pink flower color of Pink Champagne. All other traits of Empire Peach Champagne are similar to those same characteristics of Pink Champagne. Empire Peach Champagne is also distinguished from sibling cultivars Empire Gold Champagne and Empire Royal Champagne by ray floret color. In addition, Empire Gold Champagne has a 1 week later flower response.

The accompanying color photographic drawing comprises a top perspective view showing typical inflorescence and foliage characteristics of Empire Peach Champagne, with colors being as nearly true as possible with illustrations of this type.

In the following description, color references are made to The Royal Horticultural Society Colour Chart. The color values were determined between 10:00 AM and 1:00 PM on Sep. 29, 1995 under 4,000 footcandles at New Hartford, N.Y.

CLASSIFICATION:

*Botanical.*—*Dendranthema grandiflora* cv. Empire Peach Champagne.

*Commercial.*—Decorative garden mum.

Inflorescence:

A. Capitulum:

*Form.*—Flat.

*Type.*—Double.

*Diameter across face.*—6-8 cm.

B. Corolla of ray florets:

*Color: (general tonality from a distance of three meters).*—Peach.

*Color (upper surface).*—24D, blending to 179D at tips.

*Color (under surface).*—23D blending to 179D at tips.

Corolla of disc florets:

*Color (mature).*—7A.

*Color (immature).*—5A.

Reproductive organs:

*Androecium.*—Very few, present in disc florets only.

*Gynoecium.*—Present in both disc and ray florets.

Plant

A. General appearance:

*Height.*—25-35 cm. when grown in an 8" pot.

B. Foliage:

*Color (upper surface).*—147A.

*Color (lower surface).*—147B.

*Size and Shape.*—Ovate with cleft margins. Approximately 6.0 cm long, 4.5 cm wide, and 5-lobed.

It is Claimed:

1. A new and distinct cultivar of Chrysanthemum plant named Empire Pink Champagne, as illustrated and described.

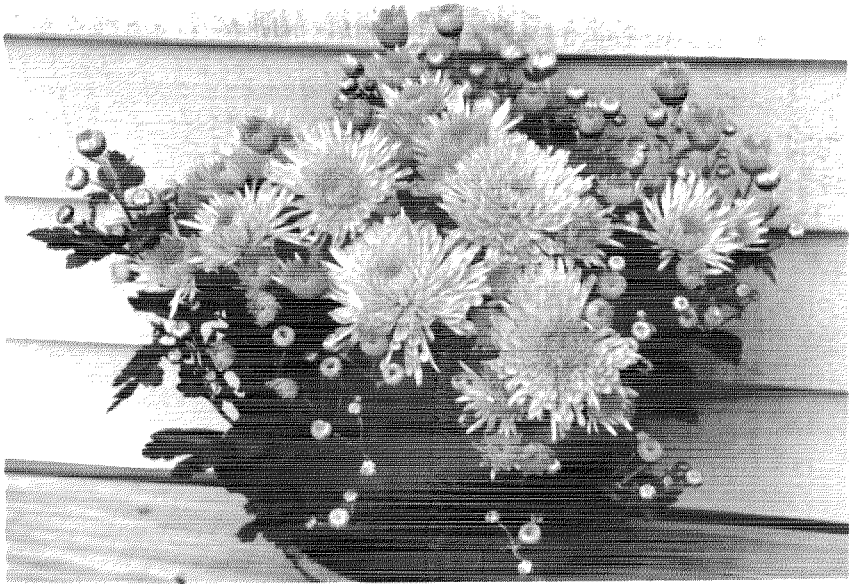

* * * * *